United States Patent [19]
Lorenz et al.

[11] Patent Number: 5,989,530
[45] Date of Patent: Nov. 23, 1999

[54] BLEACHING COMPOSITION FOR HUMAN HAIR AND PROCESS FOR ITS PRODUCTION

[75] Inventors: Heribert Lorenz, Gross-Bieberau; Frank Kufner, Darmstadt, both of Germany

[73] Assignee: Goldwell AG, Germany

[21] Appl. No.: 08/025,788

[22] Filed: Mar. 3, 1993

[30] Foreign Application Priority Data

Mar. 10, 1992 [DE] Germany .............................. 42 07 475

[51] Int. Cl.$^6$ .............................. A61K 7/07; A61K 7/135
[52] U.S. Cl. .................... 424/62; 8/101; 8/111; 252/186.25; 252/186.27; 424/DIG. 3
[58] Field of Search .................... 424/70, 71, 62, 424/DIG. 3; 8/405, 406, 101, 102, 107, 110, 111; 252/88, 94, 186.1, 186.25, 186.26, 186.27

[56] References Cited

U.S. PATENT DOCUMENTS

| | | | |
|---|---|---|---|
| 3,674,902 | 7/1972 | Kalopissis et al. ................... | 8/405 X |
| 3,847,830 | 11/1974 | Williams et al. ................... | 252/186.26 |
| 3,951,840 | 4/1976 | Fujino et al. ........................ | 252/95 X |
| 3,975,280 | 8/1976 | Hachmann et al. .................... | 252/102 |
| 4,128,494 | 12/1978 | Schirmann et al. .................... | 252/102 |
| 4,134,850 | 1/1979 | McCrudden et al. .................. | 252/95 X |
| 4,170,637 | 10/1979 | Pum ........................................ | 424/62 |
| 4,321,301 | 3/1982 | Brichard et al. ........................ | 428/403 |
| 4,522,739 | 6/1985 | Gray ...................................... | 252/95 |
| 4,844,886 | 7/1989 | Hartmann et al. ...................... | 424/62 |
| 5,258,132 | 11/1993 | Kamel et al. ........................... | 510/370 |
| 5,279,313 | 1/1994 | Clausen et al. ......................... | 132/208 |
| 5,622,691 | 4/1997 | Tricaud et al. ......................... | 424/62 |
| 5,783,175 | 7/1998 | Schultz et al. ......................... | 424/62 |
| 5,866,107 | 2/1999 | Schultz et al. ......................... | 424/62 |

*Primary Examiner*—Robert H. Harrison
*Attorney, Agent, or Firm*—Londa and Traub LLP

[57] ABSTRACT

A dustless, free-flowing powdery bleaching material for human hair which comprises a powdery composition of at least one solid peroxide compound and at least one pulverulent carrier material admixed with an oil and/or a liquid wax.

12 Claims, No Drawings

BLEACHING COMPOSITION FOR HUMAN HAIR AND PROCESS FOR ITS PRODUCTION

The present invention comprises a powdery composition for bleaching human hair presenting improved properties, and a process for the production of said composition.

Traditional blonding or bleaching compositions for human hair include at least one solid peroxide, especially a persulfate, and a powdery carrier material. Before application onto the hair, this powder is mixed with a 6 to 12% solution of hydrogen peroxide. Examples for such compositions are disclosed in the standard literature, e.g. K. Schrader, "Grundlagen und Rezepturen der Kosmetika", 2nd Edition (1989, Hüthig Buchverlag), pp. 815 to 823.

The properties of these bleaching powders, however, are not yet satisfactory. On the one hand they stir up dust when used, and on the other hand they cannot be handled exactly enough to affect the desired bleaching result.

It has now been found that a powdery composition which does not show the above-mentioned disadvantages when bleaching human hair, is achieved by the admixture of an oil and (or) a liquid wax with the carrier substance comprising at least one solid peroxide compound and at least one powdery carrier material.

This powdery composition is not only completely dustless but is also easily flowable, and allows precise dosage and may therefore be conveniently mixed with a solution of hydrogen peroxide prior to application onto the hair. These properties may be even improved in a preferred embodiment of the invention by the addition of small quantities of a non-ionic surfactant, e.g. a fatty alcohol ethoxylate or alkylphenol ethoxylates, to the powder.

DE-OS 2 023 922 already describes granular hair bleaching compositions which are produced from peroxide salts and water-soluble bonding agents, especially polyvinyl pyrrolidone.

These granules, however, are not able to solve the above mentioned problems because, on the one hand, they comprise relatively large-size particles in the region of millimeters. On the other hand problems may arise in homogeneous mixing with aqueous hydrogen peroxide. Moreover, the production of these products is relatively expensive by contrast to the bleaching powders according to the present invention which are produced in a preferred embodiment by spraying an oil or a liquid wax onto the mixture of the solid peroxide compound and the powdery carrier material.

In principle all physiologically applicable vegetable and animal oils, as well as synthetic oils, e.g. silicone oil, are suitable for the production of the bleaching powder of the present invention provided they do not affect the dissolving or dispersing properties of the aqueous hydrogen peroxide composition.

Suitable liquid waxes are particularly those having a melting point below 50° C. which may be sprayed onto the powdery premix of a solid persulfate and a carrier material.

The proportion of the oils or waxes in the composition according to the present invention is between about 2.5 to 25% by weight, especially between 5 and 15% by weight, most preferred around 8 to 12% by weight, based on the total composition.

The properties of the bleaching powder of the present invention may still be improved by admixture of low quantities of non-ionic surfactants. Particularly suitable surfactants include the well-known C12–C18-fatty alcohol polyglycol ethers, e.g. those comprising 3 to 15 EO units per mole, as well as alkylphenol polyglycol ethers, e.g. nonylphenol polyglycol ethers having about 4 to about 10 EO units per mole.

Their proportion is about 0.1 to 2.5% by weight, preferably 0.15 to 1, most preferred about 0.4 to 0.8% by weight, based on the total composition.

The blonding or bleaching composition for human hair according to the invention also comprises the known and usual ingredients in such preparations; in this context, reference is made to Schrader, l.c., to avoid repetition.

Suitable peroxides are particularly alkali persulfates such as potassium and ammonium persulfates, magnesium peroxide, urea peroxide, melamine peroxide, etc., as well as mixtures of the same.

According to a preferred embodiment of the present invention, the production of the bleaching composition is effected by spraying the oil or liquid wax onto the powder components. This takes place preferably at room temperature, i.e. the powdery ingredients should possibly not be heated over 30° C.

Another process of preparation is grinding the powdery ingredients and the oil or liquid wax, e.g. in a ball mill; however, for technical production preference is given to the above mentioned spraying procedure.

The particle size of the bleaching composition of the invention is usually below 500 micron, preferably below 400 micron ensuring excellent handling, i.e. blending with the aqueous hydrogen peroxide solution, prior to application onto human hair.

The application of the composition per se is conducted in the usual and known procedure: Mixing the powdery bleaching substance with a 6 to 12% solution of hydrogen peroxide wherein about 1 part of the powder is homogeneously mixed to about 1.5 parts of a preferably 9% hydrogen peroxide solution, and thereafter application to the hair for about 25 to about 45 minutes for processing.

The following examples illustrate the present invention.

Example 1

| | |
|---|---|
| Silica (diatomaceous earth) | 3.20% by wt. |
| Silica dioxide (pyrogenic SiO2) | 5.30 |
| Sodium carboxymethyl cellulose | 3.50 |
| Urea | 2.00 |
| Sodium lauroyl sarcosinate | 0.80 |
| Sodium stearate | 1.20 |
| Sodium carbonate | 1.00 |
| Sodium metasilicate | 6.00 |
| Starch powder | 3.50 |
| Potassium persulfate | 58.00 |
| Magnesium peroxide | 4.00 |
| Paraffin oil (Paraffinum per liquidum, DAB9) | 11.50 |

A dustfree powder is achieved which blends easily with a known 9%-solution of hydrogen peroxide in a weight proportion of 1:1.5. 99% of the particles have a diameter of less than 400 micron.

The production of the powder was effected by spraying paraffin oil onto the powder base at about 20° C. by fluidized solid technique.

Example 2

The formulation of example 1 is changed inasmuch as 0.15% by weight of a C12–C14-fatty alcohol ethoxylate (abt. 6 ethoxylate units per mol) is added while reducing the paraffin oil content accordingly.

A free-flowing dustfree product is achieved which blends excellently with a 9%-solution of hydrogen peroxide.

Example 3

The formulation of example 1 is changed inasmuch as 0.5% by weight of a nonylphenol ethoxylate (abt. 4 ethoxylate units per mol) is added while reducing the paraffin oil content accordingly. The bleaching powder achieved by this formulation is free-flowing, does not dust, and blends excellently with a 9%-solution of hydrogen peroxide.

We claim:

1. A powdered composition for the bleaching of human hair which comprises:

(A) an effective human hair bleaching amount of at least one solid peroxide compound;

(B) at least one powdered carrier material; and (C) about 2.5 to 25% by weight, based on the weight of the total composition of at least one member selected from the group consisting of an oil and a liquid wax, said member making said powdered composition dust-free and flowable.

2. The composition according to claim 1, wherein said member is present in an amount of about 5 to 15% by weight.

3. The composition according to claim 1 wherein said oil includes paraffin oil.

4. The composition according to claim 1, which further contains 0.1 to 1% by weight of a non-ionic surfactant.

5. The composition according to claim 4, wherein the non-ionic surfactant is selected from the group consisting of a fatty alcohol polyglycol ether and an alkylphenol polyglycol ether.

6. The powdery composition of claim 1, wherein the oil is selected from the group consisting of synthetic oils, vegetable oils, and animal oils.

7. The powdered composition of claim 1, wherein the wax has a melting point less than 50° C.

8. The powdered composition of claim 5, wherein the non-ionic surfactant is present in an amount of about 0.1 to 2.5% by weight.

9. The powdered composition of claim 1, wherein the solid peroxide is selected from the group consisting of potassium persulfate, ammonium persulfate, magnesium peroxide, urea peroxide, melamine peroxide, and mixtures thereof.

10. The powdered composition of claim 1, wherein the particles of the powdered composition have a diameter of less than 500 microns.

11. A process for the preparation of a powdered composition for the bleaching of human hair which comprises applying a member selected from the group consisting of an oil and a liquid wax, in an amount of about 2.5 to 25% by weight, based on the weight of the total composition, to a powdered composition comprising an effective human hair bleaching amount of at least one solid peroxide compound and at least one powdered carrier material.

12. The process of claim 11, wherein the oil member or the wax member is sprayed on the powdered composition.

* * * * *